(12) United States Patent
Hübner et al.

(10) Patent No.: US 7,501,097 B2
(45) Date of Patent: Mar. 10, 2009

(54) POSITIONING DEVICE FOR A TEST ELEMENT

(75) Inventors: Ute Hübner, Lorsch (DE); Bernd Stenkamp, Heidelberg (DE); Michael Schabbach, Weinheim (DE); Bernhard Kern, Heidelberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 661 days.

(21) Appl. No.: 10/922,638

(22) Filed: Aug. 20, 2004

(65) Prior Publication Data

US 2005/0042765 A1 Feb. 24, 2005

(30) Foreign Application Priority Data

Aug. 21, 2003 (DE) ............... 103 38 446

(51) Int. Cl.
*G01N 33/00* (2006.01)
(52) U.S. Cl. .............. 422/103; 422/68.1; 422/82.05; 422/58; 422/63; 436/169
(58) Field of Classification Search ........... 422/103, 422/55, 82.05, 68.1; 356/433, 446; 436/169
See application file for complete search history.

(56) References Cited

U.S. PATENT DOCUMENTS

| | | | | |
|---|---|---|---|---|
| 4,780,283 | A * | 10/1988 | Meinecke et al. ........ | 422/82.05 |
| 4,934,817 | A | 6/1990 | Gassenhuber | |
| 5,091,154 | A * | 2/1992 | Pauli et al. ............... | 422/63 |
| 5,281,395 | A * | 1/1994 | Markart et al. .......... | 422/82.05 |
| 5,424,035 | A | 6/1995 | Hones et al. | |
| 5,489,414 | A | 2/1996 | Schreiber et al. | |
| 5,510,266 | A | 4/1996 | Bonner et al. | |
| 5,632,410 | A | 5/1997 | Moulton et al. | |
| 5,720,924 | A | 2/1998 | Eikmeier et al. | |
| 6,335,203 | B1 * | 1/2002 | Patel et al. ............... | 436/169 |
| 6,707,554 | B1 * | 3/2004 | Miltner et al. ............ | 356/433 |
| 2003/0049168 | A1 * | 3/2003 | Patel et al. ............... | 422/58 |

FOREIGN PATENT DOCUMENTS

| | | |
|---|---|---|
| DE | 38 44 103 A1 | 7/1990 |
| DE | 197 53 847 A1 | 6/1999 |
| DE | 19854316 A1 | 10/1999 |
| EP | 0319922 A2 | 6/1989 |
| EP | 0618443 B1 | 5/1998 |
| EP | 0622119 B1 | 11/1999 |
| EP | 0738666 B1 | 7/2000 |
| EP | 1022565 A2 | 7/2000 |
| EP | 0821233 B1 | 9/2002 |

(Continued)

*Primary Examiner*—Walter D Griffin
*Assistant Examiner*—Christine T Mui
(74) *Attorney, Agent, or Firm*—Justin L. Sage

(57) ABSTRACT

The invention relates an analysis system having a positioning device for positioning a test element and a method for positioning the test element in the analysis system. The positioning device has a support surface for supporting the test element. A first switch component sits on the support element. A second switch component is positioned parallel to the first switch component. A connection is established when the second switch component is positioned in recess on the test element due to the displacement of the second switch component relative to the first switch component.

18 Claims, 5 Drawing Sheets

FOREIGN PATENT DOCUMENTS

| | | |
|---|---|---|
| EP | 0821234 B1 | 10/2002 |
| EP | 0732590 B1 | 3/2004 |
| WO | WO 97/02487 | 1/1997 |
| WO | WO 00/19185 | 4/2000 |
| WO | WO 01/89383 | 11/2001 |

* cited by examiner

POSITIONING DEVICE FOR A TEST ELEMENT

REFERENCE TO RELATED APPLICATIONS

The present application is based on and claims priority to German Patent Application No. 10338446.4, filed Aug. 21, 2003, which is hereby incorporated by reference in its entirety.

TECHNICAL FIELD

The present invention relates to a positioning device for a test element and to a method for positioning a test element in an analysis apparatus.

BACKGROUND

For analysis of samples, for example of body fluids such as blood or urine, test element analysis systems are often used in which the samples to be analyzed are located on a test element and, if appropriate, react with one or more reagents on the test element before they are analyzed. Optical evaluation, in particular photometric evaluation, of test elements is one of the most common methods for rapid determination of the concentration of analytes in samples. Photometric evaluations are generally used in the field of analysis, environmental analysis and, above all, in the area of medical diagnostics. Test elements which are evaluated by photometry have great importance in particular in the area of blood glucose diagnosis from capillary blood.

There are various forms of test elements. The main examples are square panels, also referred to as slides, at whose centre a multi-layer test field is situated. Diagnostic test elements of strip-shaped configuration are referred to as test strips. Test elements are described widely in the prior art, for example in documents DE-A 197 53 847, EP-A 0 821 233, EP-A 0 821 234 or WO 97/02487. The present invention concerns test elements of any form.

The positioning of the test elements in the test element analysis system is of great importance both for the accuracy of the analysis and for the ease of handling. One objective in carrying out analytical tests is to reduce the amounts of sample used, and to permit reliable analysis even when only small amounts of sample are present. In the area of blood glucose analysis, a drop of blood has to be taken from part of a person's body, and it is more convenient if the amount of blood needed for the test is as small as possible. A reduction in the amounts of samples is associated with decrease in the size of the test elements and in particular of the detection zones present on the test elements. To ensure an exact analysis of the sample, precise positioning of the detection zone in the test element analysis apparatus is necessary. Inaccurate spatial orientation of the test element leads directly to a decrease in the effective measurement surface and can therefore lead to a measurement error.

A large number of positioning devices for test elements are known in the prior art. EP-B 0 618 443 discloses a test strip analysis system in which a positioning of the detection zones of the test element takes place both laterally and also vertically with respect to the measurement optics, by using a bending axis transverse to its longitudinal axis and parallel to its surface. Further positioning devices for test elements can be taken for example from documents DE-A 38 44 103 or from EP-A 0 319 922.

These positioning devices cited as examples from the prior art are suitable for positioning and subsequent reliable analysis of test elements with detection zones whose size exceeds 5 mm×5 mm. If the detection zone is smaller, however, in its lateral extent, the positioning of the test elements with the aid of these positioning devices from the prior art is not sufficiently precise.

A positioning device for test elements from the prior art which permits reliable evaluation of test elements with smaller detection zones is known from document WO 00/19185. In order to hold the test element in the evaluation position, this positioning device comprises a displaceably mounted journal with a downward conically tapering end. Upon suitable positioning, the tip of the journal is situated in a recess in the test element, so that the test element is fixed in the direction of its longitudinal axis and positioned. The journal can also serve to electrically signal the presence of a test element and its positioning. For this purpose, the journal is made electrically conductive, and a contact is provided on the side of the device lying opposite it. Without a test element, the journal is pressed towards the contact by means of a spring, and an electrical contact is established between these two elements. If a test element is now inserted, it is first pushed in between journal and contact, so that the electrical contact is cancelled. When it is pushed in farther, however, the journal engages through the groove of the test element and the electrical contact closes again. A disadvantage of this positioning device is that it is costly to produce, because many electrical contact points are needed, these being produced by complex surface coating. Moreover, several component parts of the positioning device (for example the journal) assume both electrical and also mechanical functions, so that different demands are placed on the material from which they are made. For example, parts made of a combination of metal and plastic have to be used. Another considerable disadvantage of this positioning device known from WO 00/19185 is that the contact towards which the journal is pressed can be rapidly soiled by the sample. The sample located on the test element may, for example, pass through the recess in the test element and get to the contact.

Therefore, the object of the present invention is to avoid said disadvantages of the prior art and to make available a positioning device for test elements, a test element analysis system, and a method for positioning test elements, all of these permitting reliable evaluation of test elements with small detection zones. A functional separation between mechanical aspects and electrical aspects should also be permitted in the positioning device. The positioning of the test element is to be electrically signalled by low-tolerance transmission of the switching function to a remote printed circuit board.

SUMMARY

According to the invention, this object is achieved by a positioning device for a test element, comprising a support surface for the test element, a first switch component serving as a reference and sitting on the support surface or on a reference surface of the test element lying on the support surface, and a second switch component which is arranged parallel to the first switch component, sits on the test element having a position-specific surface configuration, and can be displaced perpendicular to the support surface depending on the surface configuration of the test element, the switch position of a switch depending on a displacement of the second switch component relative to the first switch component.

The switch is used to electrically signal the positioning of the test element. The switch position depends on the displacement of the second switch component relative to the first switch component. The first switch component serves as a reference. During the positioning procedure, it sits either on the support surface for the test element next to the test element or on a reference surface of the test element lying on the support surface. The plane on which the first switch component sits (support surface or reference surface) serves as a reference plane to which it is switched.

The second switch component is arranged parallel to the first switch component. It sits on the surface of the test element and is displaced relative to the first switch component by the surface configuration of the test element. The two switch components are produced and adapted to one another with precision.

The surface configuration of the test element is position-specific, i.e. at a defined position the second switch component experiences a defined displacement. Thus, the surface configuration of the test element and the arrangement of the switch components can be chosen, for example, such that in at least one position of the test element (for example the analysis position) the switch is closed by the displacement of the second switch component relative to the first, and in this way the precise attainment of the desired test element position is electrically signalled.

In a preferred embodiment of the present invention, the test element has a position-specific surface configuration which characterizes a sample application position and a sample analysis position. The sample application position is the position of the test element in which the sample, for example a drop of blood, is applied from the finger pad of a diabetic onto the test element. In the case of manual transfer of the sample onto the test element, the sample application position can, for example, be chosen such that the test element extends sufficiently far from a test element analysis system so that the sample can be transferred without any problem and reach the detection zone. In an integrated test element analysis system which in addition to an analysis apparatus also includes a system for automatic sampling, the sample application position is chosen such that the sample is transported precisely into the detection zone of the test element.

To ensure that the sample reaches the detection zone, it is necessary, both in manual and also in automatic sampling, for the sample either to be applied directly to the detection zone or to be transported into the detection zone. The latter is the case in particular in capillary slit test elements in which the sample (for example blood from the finger pad) is applied to the capillary slit and fed through the latter to the detection zone. Embodiments are also conceivable in which, for example by rubbing a fleece on an object, a solid sample is applied to the fleece, and the sample is then transported to the detection zone from the fleece by means of an auxiliary fluid, as is the case for example is some rapid drug tests. There are also chromatography test strips in which the sample is brought to the detection zone via absorbent materials.

The sample analysis position is the position of the test element in which the sample present in the detection zone is analyzed. In some test element analysis systems, the sample application position and the sample analysis position can be the same. This has the advantage that the position of the test element does not have to be altered again after sample application. In most cases, however, it is advantageous if these are two different positions of the test element. Thus, for example, a capillary slit test element can contain a shorter capillary when the detection zone after sample application is moved into a measurement position in the analysis apparatus, and the sample has therefore to travel a shorter distance in the capillary to the detection zone.

The invention also relates to a method for positioning a test element in an analysis system, with the following method steps: changing the position of a test element in the analysis system on a support surface under a spring-mounted second switch component until the second switch component, in a defined test element position, and because of the surface configuration of the test element, experiences a defined displacement relative to a first switch component sitting on the support surface or a reference surface on the test element, and closing of an electric switch on the basis of the defined displacement of the second switch component relative to the first switch component.

In the method according to the invention, the test element lies on a support surface. The change in position of the test element takes place either manually, by the person operating the analysis apparatus, or automatically, for example by a slide actuated by means of a drive unit. The test element slides under a spring-mounted second switch component. By means of the surface configuration of the test element, the second switch component is displaced relative to the first switch component which sits on the support surface of the test element or on a reference surface on the test element. The surface configuration (for example elevations or depressions) is once again position-specific, so that the attainment of at least one defined position is detected on the basis of the displacement of the second switch component relative to the first switch component and is reported back to the test element analysis system by electrical signal when the switch is closed.

The change in the position of the test element can take place in the analysis system, for example, with the aid of an automatic advance movement, and the advance movement can be turned off at a defined position of the electric switch or after a defined sequence of positions of the electric switch. A sequence of positions of the electric switch can be an open switch before insertion of a test element, a closed switch during insertion, and an open switch once again when the measurement position is reached. The automatic advance movement is turned off after this sequence of positions, that is to say when the measurement position is reached, so that the test element remains in this measurement position. However, the change in the position of the test element can also take place manually in the analysis system.

In a preferred embodiment of the present invention, the second switch component fixes the test element in a position in which the electric switch is closed. This fixing ensures that the test element does not change its position during sample application or sample analysis, even if the analysis system is shaken. Here, fixing means that the test element is pressed onto its support surface with a defined force and/or the second switch component engages with a form fit into a depression or opening in the test element, by which means an exact orientation and securing of the test element is achieved.

With the aid of the switch, the test element is positioned at least in one position in the analysis system. In a preferred embodiment of the present invention, the test element in the analysis system is pushed out of a supply container, positioned in a sample application position, positioned in an analysis position, and, if appropriate, moved into a storage container. Test elements are normally packed in a supply container to protect them from harmful environmental influences such as light, humidity or mechanical action, or to maintain them under sterile conditions. The test elements can be removed from the supply container manually or preferably by a mechanical device, and the test elements remaining in unopened chambers in the supply container are protected by separately being sealed by a foil. The test elements are removed, for example, by pushing them out of the chamber with the aid of a slide. Supply containers for analytical agents and the corresponding devices for removing the articles are described widely in the prior art and are familiar to the skilled person in a large number of embodiments. In this connection, reference may be made for example to the following documents: EP-A 0 622 119, EP-A 0 732 590, EP-A 0 738 666, U.S. Pat. Nos. 5,489,414, 5,510,266, 5,720,924, 5,632,410 and DE-A 19854316 and EP-A 1 022 565.

The supply containers, also referred to as magazines, are in most cases designed for use in measurement apparatus, in particular in compact measurement apparatus.

The removal of a test element is automated in many designs, for example in order to rule out inaccurate use or to enhance user-friendliness. In these cases the slide used to remove the test element is moved by means of a drive unit which comprises an electric drive motor and, if appropriate, a gear mechanism. Examples of conventional manual, motor-driven and automated devices for removal of test elements from supply containers are described in the documents mentioned above.

After the test element is removed from the supply container, it is positioned in the sample application position by means of a positioning device according to the invention and by the method according to the invention. After the sample has been applied, the test element is positioned according to the invention in the analysis position, if the sample application position and the analysis position differ from one another. Following analysis of the sample, the test element is either ejected from the test element analysis system, and then has to be individually stored or disposed of, or it is moved into a storage container in the test element analysis system. A further possible position in which the test element according to the invention can be positioned is a position in which a part of the test element marked out for optical reference is positioned over the optics used to qualify the detection zone in terms of ageing.

The present invention further relates to a test element analysis system comprising test elements and an analysis apparatus, the test elements having a defined position-specific surface configuration and the analysis apparatus containing a positioning device according to the invention, for positioning a test element in at least one defined position. The analysis apparatus is for example an apparatus for photometric evaluation of test elements. The test element analysis apparatus according to the invention advantageously has at least one positioning device according to the invention in order to position a test element in a sample application position and in an analysis position. In a preferred embodiment of the present invention, the test element analysis system comprises a system for withdrawing body fluid from a body part. A large number of systems for withdrawal of body fluid are known in the prior art, for example from WO 01/89383. They are used, for example, to obtain capillary blood from the finger pad, or blood or interstitial fluid from other body parts. The body fluid obtained in this way is applied to the test element in order to be analyzed in the analysis apparatus, for example for its glucose content.

In another embodiment of the present invention, the test element analysis system comprises a supply container for test elements and a withdrawal device for automatic withdrawal of at least one test element from the supply container. The test element analysis system according to the invention is preferably an integrated system with which sample collection (for example puncturing of the skin and application of blood to a test element which is removed from a supply container and is transported to a sample collection position and positioned there) and sample analysis (for example transport and positioning of the test element with the sample in the analysis position, measurement and evaluation of the relevant parameters, display of the analysis result) are fully automatic.

In a preferred embodiment of the present invention, the test element analysis system according to the invention is used for analysis of glucose in blood.

The invention is explained in more detail below with reference to the drawing, in which:

DETAILED DESCRIPTION

The following description of the preferred embodiment is merely exemplary in nature and is in no way intended to limit the invention or its application or uses.

Figure 1:
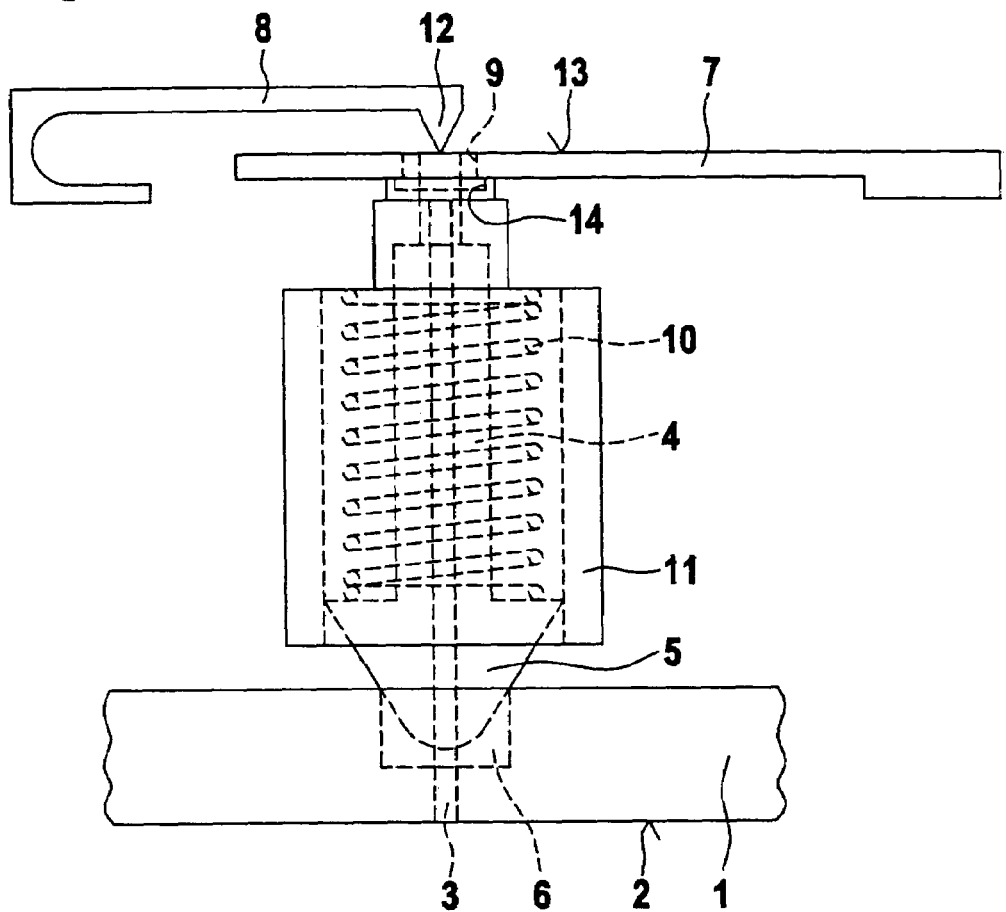
FIG. 1 shows a diagrammatic view of a positioning device according to the invention for a test element.

FIG. 1 shows a first embodiment of a positioning device according to the invention for test elements.

In this preferred embodiment of the present invention, the first switch component is a pin sitting on the support surface, and the second switch component is a displaceably mounted journal with a conically tapering end facing towards the test element, and the test element has, as position-specific surface configuration, at least one recess receiving the conically tapering end of the journal.

The test element 1, for example a test strip, is located on a support surface 2. The pin serving as first switch component 3 sits with one end on the support surface 2. The function of the second switch component 4 is assumed by a displaceably mounted journal with a conically tapering end 5 facing towards the test element 1. The first switch component 3 and the second switch component 4 are arranged parallel to one another (behind one another in FIG. 1). The second switch component 4 can be displaced perpendicular to the support surface 2. The test element 1 has at least one recess 6 which can receive the conically tapering end 5 of the second switch component 4. This recess 6 is a position-specific surface configuration of the test element 1, i.e. the recess 6 is arranged at a defined position of the test element 1 so that the test element 1 is located in a desired position, for example in a test element analysis system, as soon as the recess 6 receives the conically tapering end 5 of the second switch component 4. To position the test element 1 in this desired position, the position of the test element 1 is changed manually or automatically and pushed under the spring-mounted second switch component 4 until the second switch component 4 is located over the recess 6 and is displaced into the latter.

A switch is closed by this displacement of the second switch component 4 relative to the first switch component 3 serving as reference and sitting on the support surface 2, as a result of which the desired positioning of the test element 1 is signalled.

In the embodiment of the present invention shown in FIG. 1, the first switch component 3 determines the displacement of a spring plate, which in turn lifts a contact spring and the second switch component 4 transmits its displacement to this contact spring, so that an electric switch is closed when the contact spring 8 and the spring plate 7 touch. Maximum accuracy of positioning is afforded if the contact points of the first and second switch components 3, 4 on the contact spring 8 and spring plate 7 are very small and are located on a line arranged parallel to the spring rotation axes.

The spring plate 7 and the contact spring 8 are arranged substantially parallel to the support surface 2 of the test element 1. The first switch component 3 mechanically transmits the reference plane (in the present embodiment the plane of the support surface 2) to the spring plate 7. The second switch component 4 acts on the contact spring 8 via its end facing away from the test element 1. To do so, the second switch component 4 engages through an opening 9 in the spring plate 7. When the conically tapering end 5 of the second switch component 4 arrives at the position of the recess 6 in the test element 1, the second switch component 4 is displaced by the spring 10 and also by the spring plate 7 towards the test element 1, in which process it is guided through the guide sleeve 11. In this way, a contact edge 12 of the contact spring 8, sitting on the end of the second switch component 4 engaging through the opening 9 in the spring plate 7, nears the surface 13 in the spring plate 7. As soon as the contact edge 12 of the contact spring 8 touches the surface 13 of the spring plate 7, an electric circuit is closed and the attainment of a defined test element position is detected. The electric switch is consequently closed according to the invention by an electrical contact being established between a spring plate displaced by the first switch component and a contact spring displaced by the second switch component.

The second switch component 4 fixes the test element 1 when it engages in the recess in the test element 1, so that the test element 1 is held in this position with a defined force. Moreover, the test element 1 is very precisely aligned by the exact interaction of conical end 5 and, for example, round recess 6, since the conical end 5 centres the recess 6 about the axis of symmetry of the second switch component 4 when it is pressed into the recess 6.

The lengths of the first switch component 3 and of the second switch component 4 are precisely dimensioned in the present invention. In this way, the tolerance chain between the mechanical movement and the electrical switching function is kept as small as possible and there is minimal hysteresis. If the first switch component 3, designed for example as a pin, lies on a support surface 2 of an injection-moulded part, a high-precision switch for serial production can be realized even with inexpensive injection-moulding technology. The contact point of the first switch component 3 can additionally be used for trimming the switching point in order to homogenize parts from several cavities. The first switch component 3 prestresses the spring plate 7, as a result of which the distance to the overlying contact spring 8 is affected.

Figure 2:
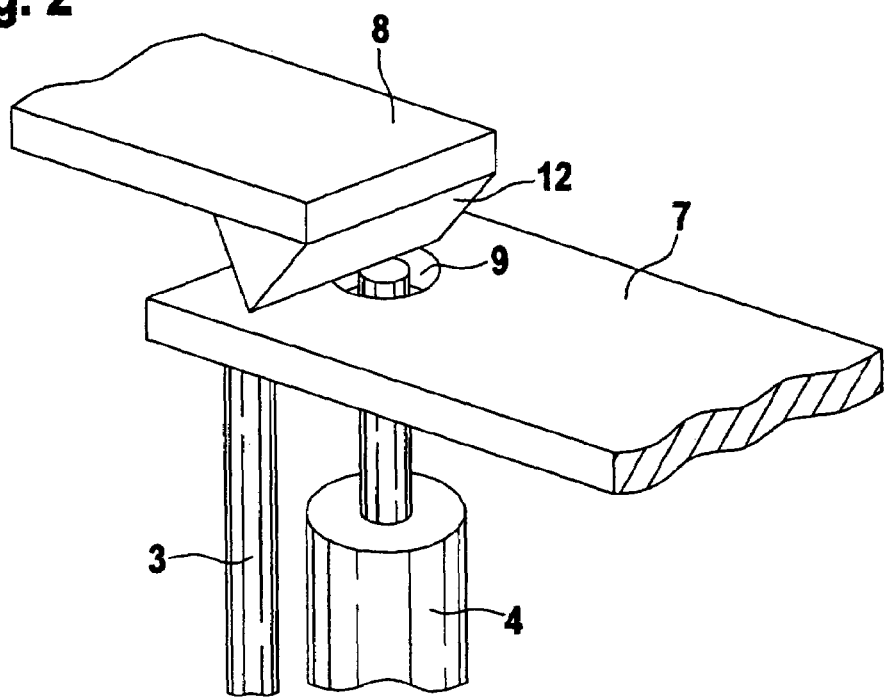
FIG. 2 shows a perspective view of a detail from FIG. 1.

FIG. 2 shows a perspective view of a detail from FIG. 1.

This detail shows the interaction of the two switch components 3, 4 with the spring plate 7 and the contact spring 8. The level of the spring plate 7 is determined by the first switch component 3 on whose end designed as contact surface it rests. The end of the first switch component 3 can be designed for example as a ring-shaped end 14 with two elevations surrounding the opening 9 (see FIG. 1), so that the spring plate 7 lies on the elevations situated on a line with switch component 4 and parallel to the spring rotation axes.

The second switch component 4 engages through the opening 9 in the spring plate 7 and lifts or lowers the contact spring 8 depending on the displacement of the second switch component 4. When the contact edge 12 of the contact spring 8 is lifted from the surface of the spring plate 7 and consequently does not touch this, the switch formed by the spring plate 7 and the contact spring 8 is in an open position. When the contact edge 12 lies on the surface of the spring plate 7, the switch is closed.

Figure 6:
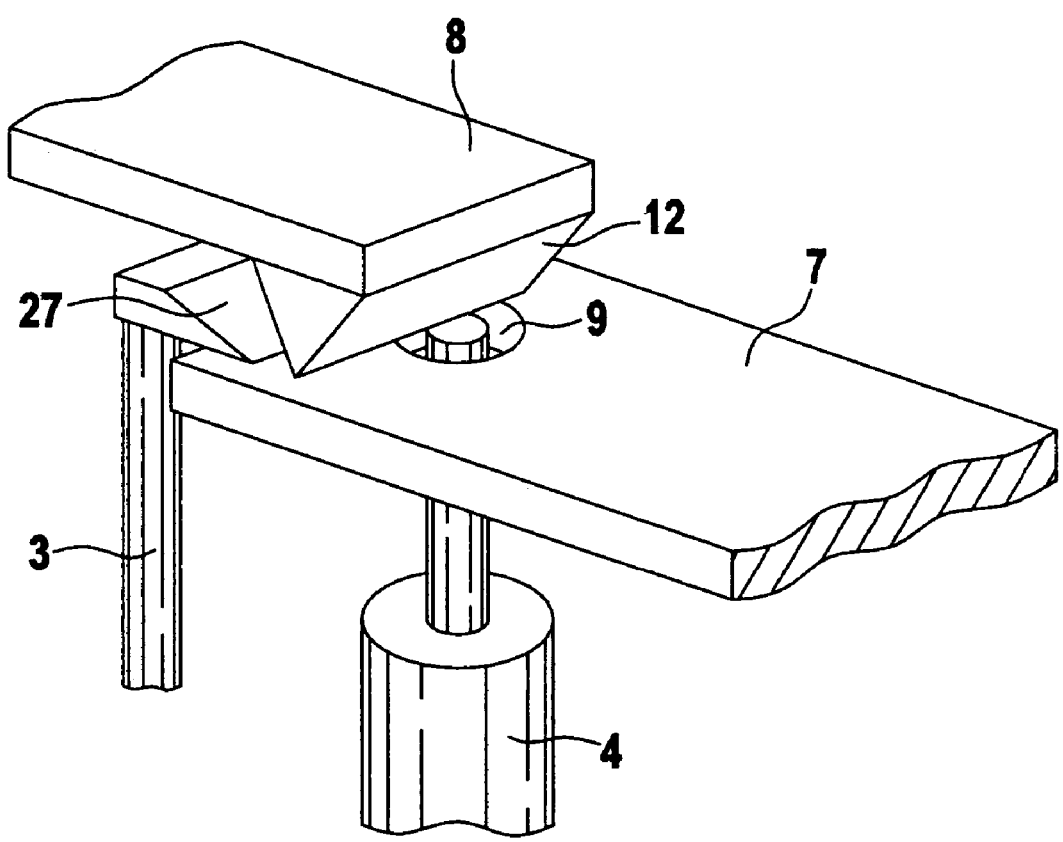
FIG. 6 shows a perspective view of a detail of a further embodiment of the present invention with spring plate and contact spring.

FIG. 6 shows a further perspective view of spring plate and contact spring in another embodiment of the present invention.

The level of the spring plate 7 is determined by the first switch component 3 which, with a contact surface present on a projection 27, rests on the spring plate 7 from above. The second switch component is arranged analogously to the embodiment of the positioning device according to the invention shown in FIG. 2. The reference numbers for the individual components in FIG. 6 correspond to those in FIG. 2.

In a preferred embodiment of the positioning device according to the invention with a spring plate 7 and a contact spring 8, in particular according to FIG. 2 or FIG. 6, the first switch component 3 determines the displacement of the spring plate 7 by touching the spring plate 7 with a contact surface 14, 27, the spring plate being prestressed in a direction to the contact surface 14, 27. The contact surface 14, 27 touches the spring plate 7 on the side facing towards the contact spring 8, on the side facing away from the contact spring 8, or on both sides of the spring plate 7.

Figure 3:
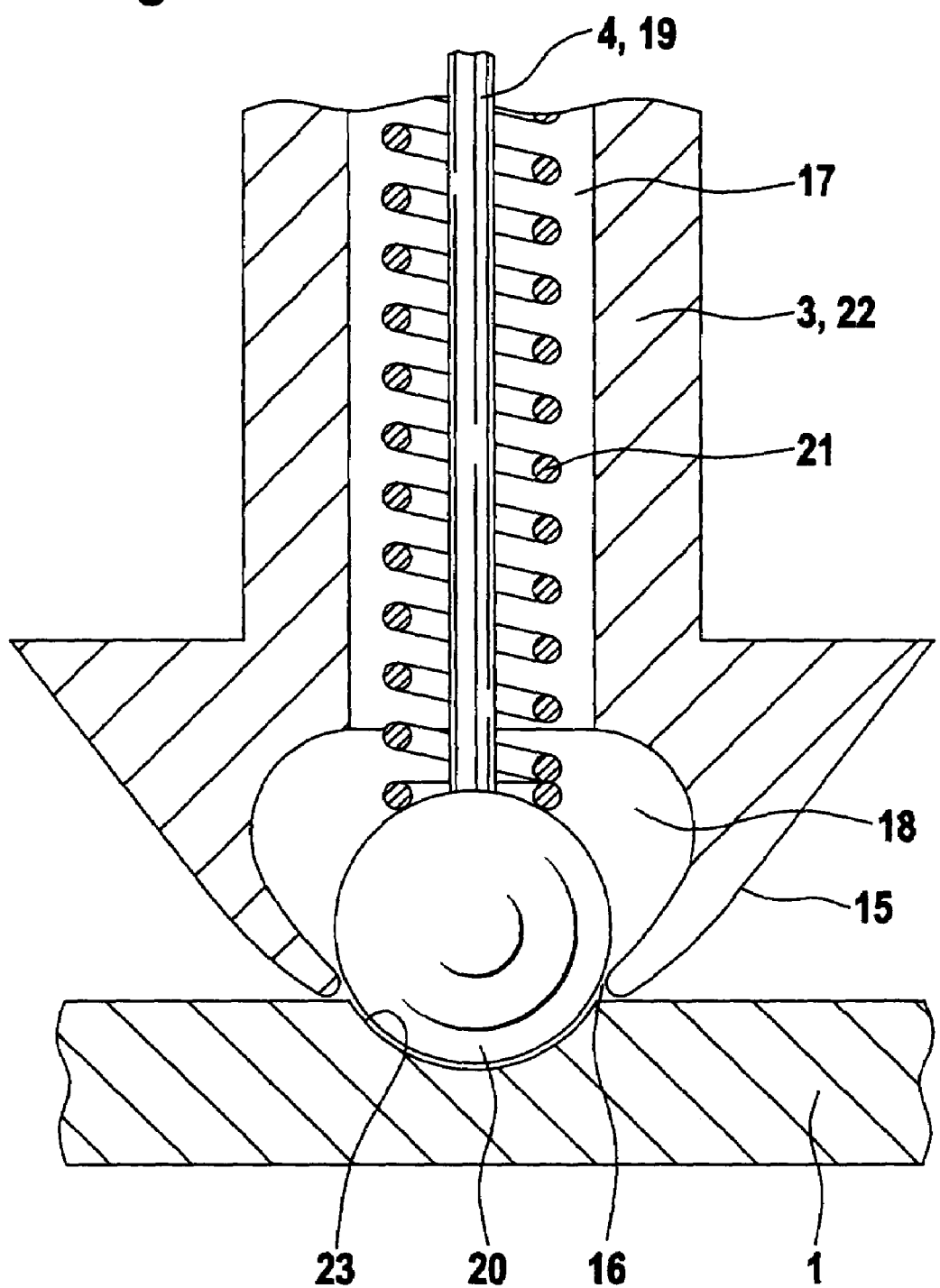
FIG. 3 shows a detail of a further embodiment of a positioning device according to the invention for a test element.

FIG. 3 shows a detail of a further embodiment of a positioning device according to the invention for test elements.

In this preferred embodiment of the present invention, the first switch component 3 is a hollow journal which sits on a reference surface of the test element 1 and which has a conically tapering end facing towards the test element 1 and with the end having an opening, and the second switch component 4 is a pin with a spherical tip, the pin being spring-mounted in the journal and the spherical tip protruding partially through the opening when the spring is extended and being pressed fully into the journal when the spring is compressed.

The first switch component 3 is here designed as a hollow journal 22 which has a conically tapering end 15 with an opening 16. In the inside of the first switch component 3 there is a longitudinal bore 17 which opens into a hollow space 18 contained in the conically tapering end 15 and adjoining the opening 16. The longitudinal bore 17 and the hollow space 18 accommodate the second switch component 4. The second switch component 4 is in this case a pin 19 with a spherical tip 20 which is spring-mounted in the longitudinal bore 17 via the spring 21 and can be displaced along the axis of symmetry of the longitudinal bore 17.

In the extended state, as shown in FIG. 3, part of the spherical tip 20 of the second switch component 4 protrudes through the opening 16 and past the conically tapering end 15 of the first switch component 3. This is the case when the surface configuration of the test element 1 permits an outward displacement, for example due to a depression 23 into which the second switch component 4 is displaced, while the first switch component 3 sits on a higher base surface of the test element 1.

In the compressed state, the spherical tip 20 is pressed fully into the conically tapering end 15 of the first switch component 3. This is the case, for example, when both the conically tapering end 15 and the spherical tip sit on a plane bottom surface of the test element 1.

A high degree of switching sensitivity is achieved by virtue of the non-linear relationship between a horizontal movement of the depression during the positioning procedure and the vertical displacement of the second switch component 4.

In this embodiment of the present invention, immersion of the conically tapering end 15 into a corresponding depression in the test element 1 effects a centering of the test element, whereas immersion of the spherical tip 20 serves for positioning. An important factor for this function is that the force with which the spherical tip 20 is pressed down is much less than the force with which the first switch component 3 is pressed down.

In this embodiment of the present invention, the surface configuration of the test element 1 is a contour which influences the displacement of the pin depending on the position of the test element 1. The contour is preferably designed as a groove of varying width and depth on the surface of the test element 1. A wide, deep portion of the groove in this case causes a considerable outward displacement of the second switch component 4, while a narrow, shallow portion of the groove allows only a slight outward displacement. Based on the extent of the displacement (depending on the displacement of the second switch component 4 relative to the first switch component 3), a defined position of the test element 1 can be detected.

Figure 4:
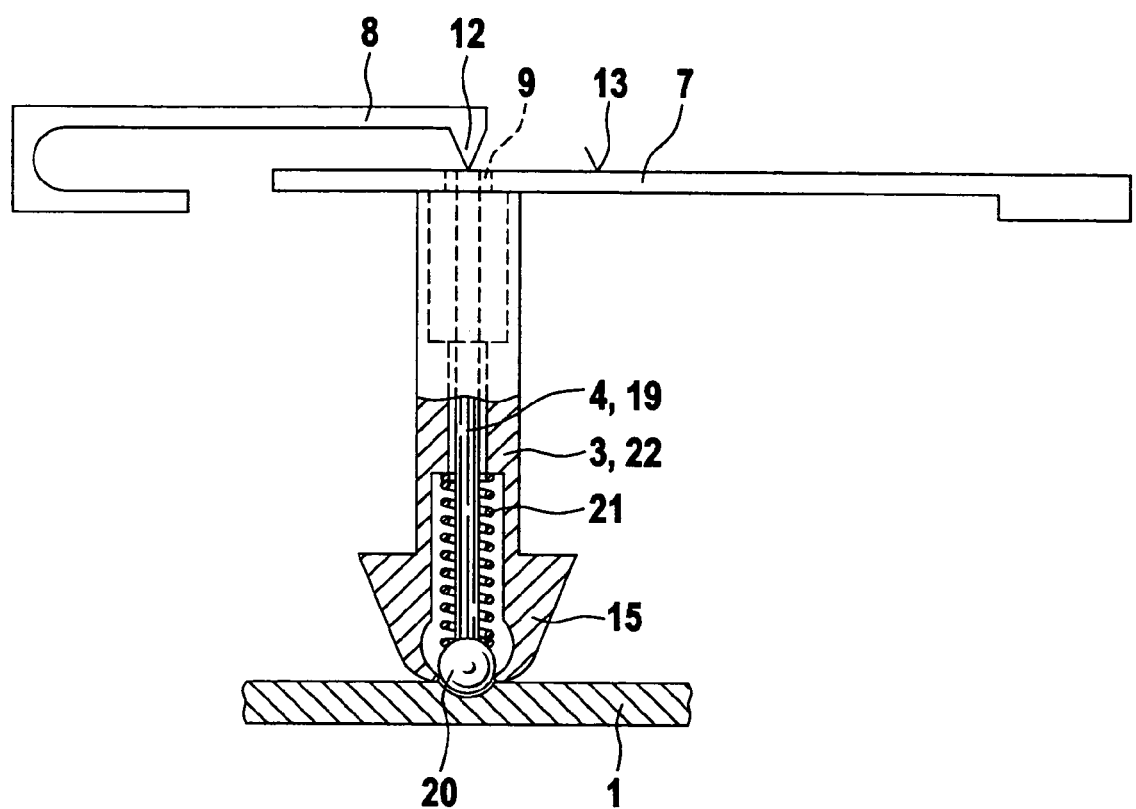
FIG. 4 shows a diagrammatic view of a further embodiment of a positioning device according to the invention for a test element.

FIG. 4 shows a further embodiment of a positioning device according to the invention for test elements.

This positioning device comprises the two switch components 3, 4 shown in FIG. 3 which are designed as a hollow journal 22 with conically tapering end 15 and as a pin 19 with spherical tip 20. Moreover, the positioning device shown in FIG. 4 comprises a spring plate 7 and a contact spring 8 which interact in the manner already described with reference to FIGS. 1 and 2. The spring plate 7 lies on the end of the journal 22 facing away from the test element 1, and the contact edge 12 of the contact spring lies on the end of the pin 19 engaging through the opening 9 in the spring plate 7. This results in a difference retainer whose switch position is obtained from the difference in displacements of the two switch components 3, 4 sliding on the surface of the test element 1.

Figure 5:
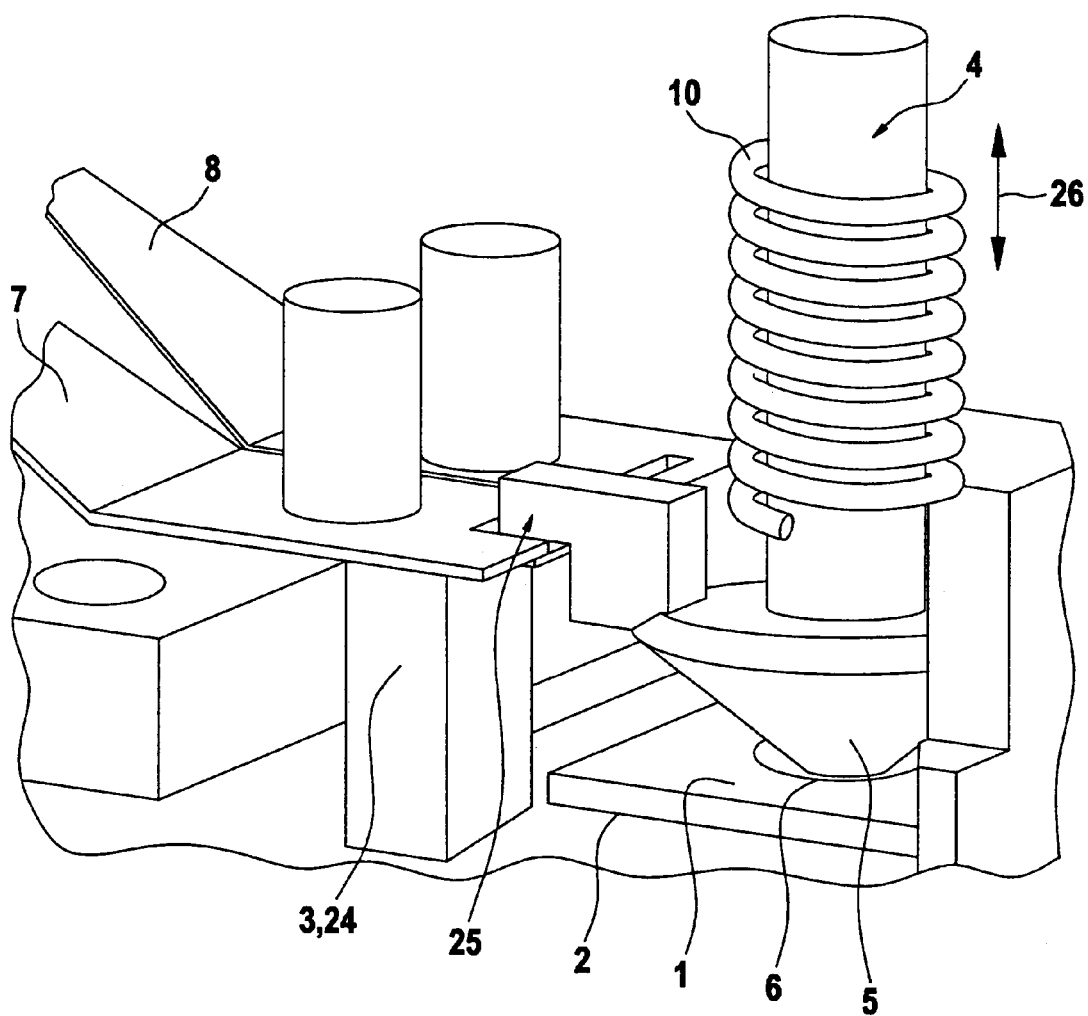
FIG. 5 shows a diagrammatic view of a further embodiment of a positioning device according to the invention for a test element.

FIG. 5 shows a further embodiment of a positioning device according to the invention for test elements.

In this embodiment, the first switch component 3 is a shoulder 24 arranged alongside the support surface 2 for the test element 1, and the second switch component 4 is a displaceably mounted journal with a conically tapering end 5 facing towards the test element 1. The test element 1 has, as position-specific surface configuration, at least one recess 6 receiving the conically tapering end 5 of the journal. The shoulder 24 is of cuboid shape. It would also be conceivable, for example, for the shoulder 24 to have a step-shaped design. In this embodiment, the shoulder 24 and the support surface 2 for the test element 1 are made in one piece.

The second switch component 4 is mounted displaceably in the direction of the arrows 26 and is moved by the spring 10 towards the test element 1. The electric switch is opened as soon as the contact spring 8 is lifted from the spring plate 7 in the direction of the support surface 2 by the lateral projection 25 of the second switch component. This is the case, for example, when the conically tapering end 5 of the journal engages in a recess 6 of the test element, as is shown in FIG. 5, or when there is no test element 1 present on the support surface 2. The spring plate 7 and the contact spring 8 form contacts which are made, for example, as flexible metal parts and are electrically connected to a microcontroller (not shown) for signal evaluation As any person skilled in the art will recognize from the previous description and from the figures and claims, modifications and changes can be made to the preferred embodiment of the invention without departing from the scope of the invention as defined in the following claims.

LIST OF REFERENCE NUMBERS 1 test element
2 support surface
3 first switch component
4 second switch component
5 conically tapering end of second switch component
6 recess in test element
7 spring plate
8 contact spring
9 opening in spring plate
10 spring
11 guide sleeve
12 contact edge of contact spring
13 surface of spring plate
14 ring-shaped end of first switch component
15 conically tapering end of first switch component
16 opening in conically tapering end of journal
17 longitudinal bore
18 hollow space
19 pin
20 spherical tip
21 spring
22 journal
23 depression
24 shoulder
25 projection
26 arrows
27 projection

What is claimed is:

1. An analysis system having a positioning device for a test element, the positioning device comprising:
    a support surface to support the test element;
    a position-specific surface configuration on the test element;
    a first switch component serving as a reference; wherein the first switch component is sitting on the support surface adjacent the test element or on a reference or a reference surface of the test element arranged on the support surface;
    a second switch component which is arranged parallel to the first switch component, wherein the second switch component sits on the position-specific surface configuration, such that the second switch component can be displaced perpendicular to the support surface depending on the configuration of the test element; and
    a switch, wherein the switch can be changed from an off position to an on position depending on a displacement of the second switch component relative to the first switch component and a plane on which the first switch component sits, said plane serving as a reference plane with respect to which the switching operation is performed.

2. The system according to claim 1, wherein the first switch component is a pin which sits on the support surface.

3. The system according to claim 1, wherein the second switch component is a displaceably mounted journal with a conically tapering end facing towards the test element.

4. The system according to claim 3, wherein the position-specific surface configuration on the test element is at least one recess receiving the conically tapering end of the journal.

5. The system according to claim 1, wherein the first switch component is a shoulder arranged alongside the support surface.

6. The system according to claim 5, wherein the shoulder is cuboid or step-shaped.

7. The system according to claim 5, wherein the shoulder and the support surface are made in one piece.

8. The system according to claim 1, wherein the test element has a reference surface lying on the support surface, such that the first switch component is sitting on the reference surface.

9. The system according to claim 8, wherein the first switch component is a hollow journal which sits on the reference surface of the test element and has a conically tapering end facing towards the test element and with an opening, and the second switch component is a pin with a spherical tip, the pin being spring-mounted in the journal, and the spherical tip protruding partially through the opening and past the conically tapering end of the journal when the spring is extended, and being pressed fully into the journal when the spring is compressed.

10. The system according to claim 9, wherein the surface configuration of the test element is a contour that influences the displacement of the pin depending on the position of the test element.

11. The system according to claim 10, wherein the contour is designed as a groove varying in width and depth on the surface of the test element.

12. The system according to claim 1, wherein the first switch component determines the displacement of a spring plate, and the second switch component transmits its displacement to a contact spring, an electric switch being closed when the contact spring and the spring plate touch.

13. The system according to claim 12, wherein the second switch component engages through an opening in the spring plate.

14. The system according to claim 12, wherein the second switch component has a lateral projection via which the second switch component transmits its displacement to the contact spring.

15. The system according to claim 12, wherein the first switch component determines the displacement of the spring plate by touching the spring plate via a contact surface, the spring plate being prestressed in a direction to the contact surface.

16. The system according to claim 15, wherein the contact surface touches the spring plate on the side facing towards the contact spring, on the side facing away from the contact spring or on both sides of the spring plate.

17. The system according to claim 1, wherein the test element is a capillary slit test element.

18. The system according to claim 1, wherein the test element has a position-specific surface configuration which characterizes a sample application position and a sample analysis position.

* * * * *